United States Patent [19]

Park

[11] Patent Number: 5,057,111
[45] Date of Patent: Oct. 15, 1991

[54] NON-STRESS-SHIELDING BONE FRACTURE HEALING DEVICE

[76] Inventor: Joon B. Park, 6 Lake Pointe Rd., R.R. #6, Iowa City, Iowa 52240

[21] Appl. No.: 116,497

[22] Filed: Nov. 4, 1987

[51] Int. Cl.$^5$ ................................................. A61F 5/04
[52] U.S. Cl. ......................................... 606/69; 606/70
[58] Field of Search ......... 128/92 YP, 92 YL, 92 YE, 128/92 YV, 92 ZN, 92 R, 92 Z; 606/69, 70, 71, 57

[56] References Cited

U.S. PATENT DOCUMENTS

| | | | |
|---|---|---|---|
| 1,025,008 | 4/1912 | Miner | 128/92 YL |
| 3,552,389 | 1/1971 | Allgower | 128/92 |
| 3,596,656 | 8/1971 | Kaute | 128/92 |
| 3,739,773 | 6/1973 | Schitt et al. | 128/92 BC |
| 3,779,240 | 12/1973 | Kondo | 128/92 D |
| 4,388,921 | 6/1983 | Sutter et al. | 128/92 B |
| 4,408,601 | 10/1983 | Wenk | 128/92 D |
| 4,513,744 | 4/1985 | Klaue | 128/92 D |
| 4,711,234 | 12/1987 | Vives et al. | 128/92 YP |

OTHER PUBLICATIONS

*Journal of Bone and Joint Surgery*, "A Comparison of Cortical Bone Atrophy Secondary to Fixation with Plates with Large Differences in Bending Stiffness," vol. 58-A, No. 1, (Mar. 1976), pp. 190-195, Woo, et al.

*Primary Examiner*—Robert A. Hafer
*Assistant Examiner*—Michael Brown
*Attorney, Agent, or Firm*—Dority & Manning

[57] ABSTRACT

A non-stress-shielding bone fracture healing compression device is to be used with screws, pins or nails for attaching the device to bone tissue. A rigid plate has at least two openings therethrough for purposes of attaching the plate to the bone with screws, pins or nails. At least one of the openings is a relaxation opening that has an opening surface shaped at least in part as a truncated spherical section and has an entrance hole through the top of the plate and an exit hole through the bottom of the plate. The polymer member is shaped to conform to the opening surface and to form circular entrance and exit holes concentric with the respective relaxation opening surface entrance and exit holes. The polymer member can be either resorbable material or viscoelastic material and can be configured to cover either all or less than all of the opening surface of the relaxation opening. When the plate is in use, the resorbable material is absorbed into the body to lessen contact between the pin, for example, and the plate, thereby reducing the load carried by the plate and pin and increasing the load carried by the bone attached to the plate and pin. When viscoelastic material is used, the stress gradually causes this material to creep away from contact with the pin, for example, and the load carried by the plate and pin is reduced while the load carried by the bone is increased.

19 Claims, 1 Drawing Sheet

NON-STRESS-SHIELDING BONE FRACTURE HEALING DEVICE

BACKGROUND OF THE INVENTION

The present invention relates to bone fracture compression plates, and in particular to non-stress-shielding plates.

Compression plates typically are attached to the bone by screws to transfer the load from the bone to the plate through the screws and force the broken ends of the bone together. Refinements to this basic device have been made. Other typical fracture fixation compression devices are disclosed in U.S. Pat. Nos. 4,513,744; 3,779,240; and 3,552,389.

When a conventional bone fracture compression plate made of high modulus 316L stainless steel (200 GPa; $30 \times 10^6$ psi) relative to cortical bone (15 GPa) is used, this results in stress-shielding the bone under the plate and is believed to cause an osteoporosis that weakens the bone under the plate. Relieving the bone from carrying a load over an extended period of time is believed to contribute to the development of this type of osteoporosis, also known as osteopenia. When the plate and screws are removed from the healed bone, the bone may refracture due to the weakening which resulted from the development of osteoporosis or osteopenia.

Attempts to solve this problem have included the fabrication of the fracture plates from materials that are less rigid than 316L stainless steel. For example, titanium alloys, composites, and resorbable materials have been tried. However, each of these materials presents additional problems.

Fracture plates require screw holes which tend to acquire nicks and notches from contact with the screws. Titanium alloys require heat treatment for strengthening, but such treatment lowers the shear strength, thus rendering the plate particularly sensitive to nicking and notching. The nicks and notches become sites for the development of undesirable corrosion.

An investigation using graphite fiber reinforced polymethylmethacrylate (GFMM) as the plate material is reported in Woo et al, "A Comparison of Cortical Bone Atrophy Secondary to Fixation with Plates and Large Differences in Bending Stiffness," *J. Bone Jt. Surg.*, Vol. 58A, pp. 190-195 (1976). Composites present the usual problems of debonding, low fatigue limit, etc.

Bioresorbable bone plates have been investigated in Christal et al, "In vivo fate of bioresorbable bone plates in long-lasting poly (L-lactic acid)," p. 279, *Trans. Second World Congress on Biomaterials*, Apr. 27-May 1, 1984, Washington, D.C. The main problems associated with resorbable bone plates made of polyglycolic acid (PGA) or polylactic acid (PLA) polymers are the release of large amounts of the polymer residues into the body. It is not yet proven whether these polymer residues produce any side effects. However, the precise control of the dissolution rate of these polymers over the entire plate is difficult, if not impossible, due to many factors. Moreover, the screws cannot be made from these materials because these materials lack the requisite torsional strength. Hence, conventional metal screws must be used, and a secondary operation to remove the screws cannot be avoided, even when the plates are made of resorbable materials.

Other attempts at solving the stress-shielding problem include the use of non-conventional types of fracture plates.

A distinction is made between compression devices disclosed above which are removed at a certain point during the healing process, and non-compression "conventional" fixation devices. One difference between a compression plate and a non-compression fixation device is the shape of the holes used in securing the respective devices to the bone. Non-compression fixation devices typically use holes having a generally frustoconical profile, while compression plates use holes having a more spherical profile. This is because the former is intended to remain fixed, and the latter is intended to allow the screws to be offset or directed at an angle into the bone. For example, in U.S. Pat. No. 3,596,656 to Kaute, a non-compression fixation device comprises a frustoconical shape bore and a similarly shaped washer which can be formed of high density, high molecular weight polyethylene. The washer is fitted into the countersunk portion of each plate bore to avoid corrosion and electrical effects caused by contact between the bore surface and the screw inserted through the bore into the bone. The washer can include a coaxial straight-sided tubular neck part that terminates spaced from the backface of the plate and that has an outer diameter smaller than the bore diameter and an inner diameter larger than the diameter of the screw shank.

SUMMARY OF THE INVENTION

It is a principal object of the present invention to provide a device that aids the healing of bone fractures without promoting the development of osteoporosis or osteopenia.

It also is an object of the present invention to aid the healing of bone fractures without stress-shielding the fractured bone during the healing process so as to cause or contribute to the development of osteoporosis or osteopenia.

A further object of the present invention is to provide a device to aid the healing of bone fractures and that gradually transfers the stress load from the device to the healing bone so as to avoid or lessen the severity of osteoporosis or osteopenia.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the non-stress shielding bone fracture compression healing device of the present invention is to be used with a means for attaching the device to bone tissue having a fracture therein, the attaching means having an outer surface facing its environment. The device of the present invention comprises a rigid plate having a top surface, a bottom surface, and a predetermined region that is intended to be disposed so as to extend across the bone fracture. The top and bottom surfaces generally are on opposite sides of the plate. At least two openings are defined in the plate and extend through the plate from the top surface to the bottom surface. At least one of these openings is disposed on one side of the predetermined plate region and at least a second of the openings is disposed on the opposite side of the predetermined plate region. In this way, there is intended to be at least one opening on each side of the fracture when the plate is attached to the bone.

A plate opening surface defines the boundary of each plate opening and defines this boundary through the plate from the top surface to the bottom surface.

At least one of the plate openings is a relaxation opening. Each relaxation opening has an entrance hole through the top plate of the surface and an exit hole through the bottom plate surface. The opening surface of each relaxation opening is preferably configured as a sphere truncated at the entrance hole and at the exit hole.

The invention further includes means for producing a separation between at least a portion of the outer surface of the attaching means and at least a portion of the opening surface of each relaxation opening when the attaching means extends through the relaxation opening to attach the plate to the bone tissue. The separation producing means has a thickness profile that determines the nature of the separation between the outer surface of the attaching means and the opening surface of the relaxation opening. The thickness profile of the separation producing means is controllable to change gradually over a predetermined period of time. The gradual change in the thickness profile causes a gradual transfer of load from the plate and attaching means to the bone attached to the plate.

As embodied herein, the separation producing means preferably comprises a polymer member configured to extend continuously from the top surface to the bottom surface of the plate to cover the plate opening surface that will carry part of the load when the device is in use. The polymer member has a plate contacting surface that seats on a continuous portion of the plate opening surface that extends from the top surface of the plate to the bottom surface of the plate. This plate contacting surface contacts the plate opening surface which will carry part of the load when the device is in use. The polymer member also has an attaching means contacting surface that is disposed to contact the attaching means when the device is used for bone fracture healing. The attaching means contacting surface is configured to follow the contour of at least a continuous portion of the outer surface of the attaching means. This portion of the outer surface of the attaching means is the portion that resides within the relaxation opening when the attaching means extends through the relaxation opening to attach the plate to the bone. All of the plate contacting surface of the polymer member is disposed against at least a portion of the plate opening surface and facing generally oppositely to the attaching means contacting surface of the polymer member. The thickness profile of the polymer member is preferably uniform at the initial stage of its reception into the relaxation opening.

The present invention includes both a full lining embodiment and a partial lining embodiment. In both embodiments, the surface that contacts the attaching means has a generally spherical profile. In the full lining embodiment, the polymer member attaching means contacting surface alone provides this spherical profile. In the partial lining embodiment, the spherical profile is formed partly by the opening surface of the relaxation opening and partly by the attaching means contacting surface of the polymer member.

Preferably, the polymer member is formed either of viscoelastic material or resorbable material. When formed of a viscoelastic material, the polymer is preferably ultra high molecular weight polyethylene (UHMWPE) of a type which has been approved by the U.S. Food & Drug Administration for use in prosthetic joints. When formed of a resorbable material, the polymer member is preferably formed of the type of polyglycolic acid or polylactic acid which is used to fabricate resorbable sutures that have been approved by the U.S. Food and Drug Administration.

The means used to attach the device to bone tissue preferably includes screws, pins, nails, or the like. These attaching means are inserted through the plate opening and imbedded into bone tissue to attach the plate firmly to the bone tissue. Contact between the attaching means and the plate is effected indirectly via the polymer member over those portions of the plate opening surface covered by the polymer member. In addition, part of the load carried by the plate and attaching means is also carried by the polymer member.

When the device is initially attached to the bone to aid healing of the bone fracture, the device carries most of the load that otherwise would be carried by the bone in normal use. This relieves the bone from experiencing stress under load during the initial stages of healing. As the bone mends and is able to carry some load and endure some stress, the polymer member acts to transfer part of the load from the plate to the bone. This phenomenon is believed to occur in two different ways depending upon the composition of the polymer member.

When the polymer member is composed of viscoelastic material, this material gradually deforms under pressure. Thus, as the plate is subject to load, the plate and the attaching means subject the polymer member therebetween to pressure that causes the polymer member to creep out of the relaxation plate opening and away from the attaching means. Over time, the creeping phenomenon changes the separation between the opening surface and the outer surface of the attaching means. For example, the creeping phenomenon changes the thickness profile of the polymer member by decreasing the polymer member thickness between the attaching means contacting surface and the plate opening surface. The reduction in the thickness profile of the polymer member causes a transfer of load from the plate to the healing bone.

The creeping phenomenon is predictable so that the transfer of load can be effected in a controlled manner. The relaxation phenomenon associated with the creeping occurs gradually, and thus the transfer of load from plate to bone also occurs gradually over a matter of weeks or months until the entire load is transferred from the plate to the bone. See TABLES 1 and 2.

When the polymer member is composed of resorbable material, this material gradually is absorbed into the body and creates a polymer member having a reduced thickness profile between the outer surface of the attaching means and the plate opening surface. This reduced polymer member thickness profile changes the separation between the opening surface of the relaxation opening and the outer surface of the attaching means. This change in separation causes the bone to carry some of the load previously carried by the plate. This load subjects the bone to stress. As the thickness profile of the polymer member diminishes over time due to absorption of same, the amount of load carried by the bone commensurately increases, as does the stress applied to the bone. Eventually, enough of the entire polymer member is absorbed by the body so that the plate is attached so loosely to the bone that the plate no longer carries any load.

The rigid plate and the pins, screws and nails comprising the attaching means preferably are formed of a corrosion resistant metal such as stainless steel, a cobalt-chromium-molybdenum alloy, or a titanium alloy. Other materials, such as carbon composites or aluminum, can be used so long as they possess the requisite strength and rigidity and are biocompatible, i.e., acceptable to the tissue of the body in which the device is used.

The accompanying drawings, which are incorporated in and constitute a part of this specification, illustrate embodiments of the invention, and together with the description, serve to explain the principles of the invention.

DESCRIPTION OF THE PREFERRED EMBODIMENTS

Reference will now be made in detail to the present preferred embodiments of the invention, examples of which are illustrated in the accompanying drawings.

In accordance with the present invention, there is provided a non-stress-shielding bone fracture compression healing device to be used with means for attaching same to bone tissue having a fracture therein. As embodied herein, the means for attaching the device to bone tissue preferably comprises screws, nails, pins, or the like. One end of the attaching means is to be embedded into the bone, while the opposite end of the attaching means is to rest firmly in contact with the device of the present invention to attach same to the bone. The attaching means has an outer surface which faces its environment. Preferably, the screws, nails, pins, or the like comprising the attaching means are formed of any sufficiently strong and rigid material that is also biocompatible, i.e., acceptable to the tissue which will come into contact with these items. For example, stainless steel or other corrosion resistant metals such as a cobalt-chromium-molybdenum alloy or a titanium alloy possess the requisite properties.

Figure 1:
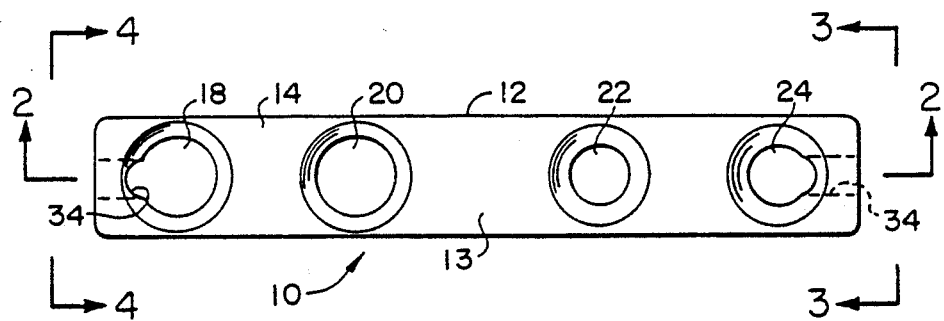
FIG. 1 is a top plan view of a preferred embodiment of a component of the present invention.
Figure 2:
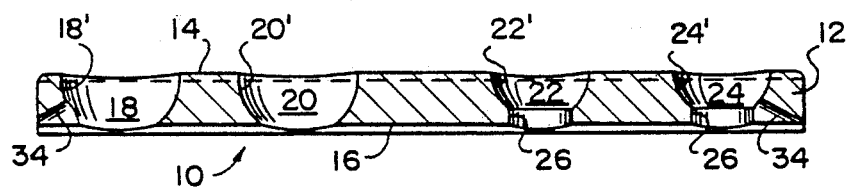
FIG. 2 is a side cross-section taken along the lines 2—2 of FIG. 1.

The device of the present invention is indicated generally in FIGS. 1 and 2 by the designating numeral 10, and includes a rigid plate 12 having a top plate surface 14 and a bottom plate surface 16. In use, bottom surface 16 is configured to rest against the bone 17 in FIG. 5 which is to be healed, and top surface 14 is disposed generally opposite bottom surface 16. Bottom surface 16 is preferably contoured, or curved as illustrated for example in FIGS. 2–4, for accommodating the profile of the bone surface to which plate 12 is to be attached. Plate 12 must be formed of a material sufficiently rigid to carry the load normally carried by the bone to which the plate is to be attached to aid healing of the bone fracture. Preferably, plate 12 is formed of a corrosion resistant metal such as stainless steel, a cobalt-chromium-molybdenum alloy or a titanium alloy. Plate 12 also can be formed of any sufficiently strong and rigid material that is also biocompatible.

Typically, compression plates such as the present invention have a height dimension that is the plate thickness in the direction normal to the surface of the bone to which the plate is attached. As shown in FIG. 2 for example, the height dimension of plate 12 is the shortest distance between top surface 14 and bottom surface 16. The length dimension (longer dimension in FIG. 1 for example) of the plate is the dimension parallel to the longitudinal axis of the bone to which the plate is attached, and the width dimension (shorter dimension in FIG. 1 for example) is the dimension normal to the length dimension. Typically, a compression plate will be provided with openings therethrough that are disposed along the length of the plate so that when the plate is situated on the bone to be healed, there will be openings on both sides of the fracture so that the attaching means can be secured to the fractured bone on opposite sides of the site of the fracture.

In the embodiment of the present invention illustrated in FIGS. 1–2, plate 12 contains four openings 18, 20, 22 and 24. All four openings extend completely through plate 12 from top surface 14 to bottom surface 16. The openings are preferably disposed along the length of plate 12 so that the fracture can be situated symmetrically between two of the openings and so that an equal number of openings will be situated on each opposite side of the fracture. In the embodiment of plate 12 shown in FIGS. 1 and 2 for example, the fracture likely would be situated between openings 20 and 22 and a portion 13 of plate 12 between openings 20 and 22 is the predetermined portion of plate 12 that is intended to extend across the fracture when the plate is attached to the bone.

Plate removal slots 34 are provided adjacent the ends of plate 12 and extend into openings 18, 22. Plate removal slots 34 allow for insertion therein of a plate removal instrument (not shown) such that after removal of the attaching means, plate 12 may be removed from a bone by prying or pulling with the plate removal instrument.

In accordance with the present invention, each opening has an opening surface that defines the boundary of that particular opening through the plate from the top plate surface to the bottom plate surface. As embodied herein and shown in FIG. 2 for example, opening surfaces 18', 20', 22', and 24' are shown in a cross-sectional view for respective openings 18, 20, 22, and 24. As embodied herein and shown for example in FIG. 6a, opening surface 48' is shown in a cross-sectional view for plate opening 48.

In yet further accordance with the present invention, at least one of the plate openings is a relaxation opening. As embodied herein and shown for example in FIGS. 1, 2, 4, 5, 6, and 6a, plate openings 18, 20, and 48 are relaxation openings. Each relaxation opening 18, 20, 48 has an entrance hole 18a, 20a, 48a, respectively, through top plate surface 14 and a respective exit hole 18b, 20b, 48b through bottom plate surface 16.

In the embodiment of FIGS. 1-5, each opening surface 18', 20' of each relaxation opening 18, 20 is preferably configured as a sphere truncated at the respective entrance hole 18a, 20a and exit hole 18b, 20b. Thus, in the embodiment of FIGS. 1-5, at least one plate opening is a relaxation opening which defines a truncated spherically shaped opening that is formed so that the boundary surface of the plate opening is defined by a particular radius.

In some embodiments of the present invention, all plate openings will be shaped as relaxation openings 18, 20, or 48. However, in one preferred embodiment of the invention illustrated in FIGS. 1-5, only plate openings 18 and 20 are shaped as truncated spheres.

Figure 4:
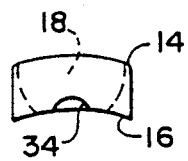
FIG. 4 is a side elevation view taken along the lines 4—4 of FIG. 1.

As shown particularly in FIGS. 2 and 4, plate openings 22 and 24 are conventional compression plate openings configured in a manner that is typical of the plate openings of conventional compression plate devices for setting bone fractures. Openings 22 and 24 are shaped as truncated spheres having a cylindrically shaped extension portion 26 normal to the surface of the bone to which plate 12 is intended to be attached.

The present invention requires at least one relaxation plate opening configured as plate openings 18, 20, or 48 illustrated in the drawings. However, it is preferred that the relaxation openings be provided so that they are situated symmetrically both with respect to any conventionally shaped plate openings and relative to the site of the bone fracture. Thus, as shown in FIGS. 1 and 2, relaxation openings are provided on one side of plate 12, while conventional compression plate openings are provided on the opposite half of plate 12. In another alternative embodiment of the present invention, a relaxation opening and a conventional compression plate opening are provided on each half of plate 12, and either both similarly shaped openings can be situated closest to the center of plate 12 or one of each differently shaped opening can be situated closest to the center of plate 12 but on opposite halves thereof.

As shown in FIG. 2, plate opening surfaces 18', 20' define the boundary of relaxation openings 18, 20, respectively, through plate 12 from top surface 14 to bottom surface 16. Relaxation openings 18, 20 preferably are formed symmetrically about an axis 23 (FIG. 5) therethrough.

In further accordance with the present invention, means are provided for producing a separation between at least a portion of the outer surface of the attaching means and the plate opening surface of each relaxation opening when the attaching means extends through the relaxation opening to attach the plate to the bone tissue. The separation producing means has a thickness profile that is controllable to change this separation gradually over a predetermined period of time. The gradual change in the thickness profile causes a gradual transfer of load from the plate and attaching means to the bone attached to the plate.

The present invention includes both a full lining embodiment and a partial lining embodiment. In both embodiments, the surface that contacts the attaching means has a generally spherical profile. In the full lining embodiment, an example of which being shown in FIG. 5, the polymer member attaching means contacting surface alone provides this spherical profile. In the partial lining embodiment, an example of which being shown in FIGS. 6 and 6a, the spherical profile is formed partly by the opening surface of the relaxation opening and partly by the attaching means contacting surface of the polymer member.

Figure 5:
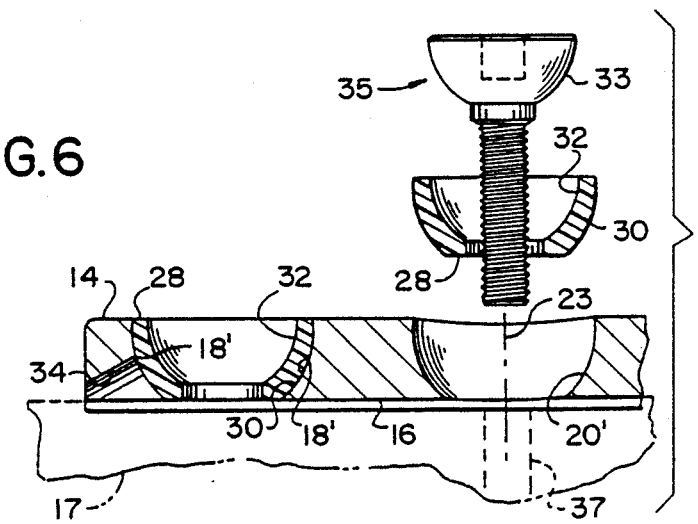
FIG. 5 is a cross section view, with parts cut away, of a preferred partial embodiment of the present invention.

As embodied herein and shown for example in FIG. 5, the separation producing means preferably comprises a polymer member 28. As shown in FIG. 5, polymer member 28 is configured to extend continuously from top surface 14 to bottom surface 16 when polymer member 28 is disposed flush against a plate opening surface 18', 20' of a relaxation opening 18, 20. As shown in FIG. 6a, a polymer member 50 is configured to extend continuously from top surface 14 to bottom surface 16 when polymer member 50 is disposed flush against a portion of plate opening surface 48' of relaxation opening 48.

Polymer member 28 has a plate contacting surface 30 that is configured to contact a plate opening surface 18', 20' of a respective relaxation opening 18, 20 in an uninterrupted fashion from the top plate surface to the bottom plate surface. When plate contacting surface 30 of polymer member 28 is disposed against plate opening surface 18' for example, there initially are preferably no gaps or voids between plate contacting surface 30 and plate opening surface 18'. In other words, as shown in FIG. 5, all of plate contacting surface 30 of polymer member 28 is preferably disposed against at least a continuous portion of plate opening surface 18'.

As shown for example in FIG. 5, polymer member 28 also has an attaching means contacting surface 32 which is disposed to contact the attaching means, such as a screw, when device 10 is in use for bone fracture healing. Attaching means contacting surface 32 is preferably configured to conform to at least the continuous portion of the outer surface of the attaching means that resides within the relaxation opening when the attaching means extends through the relaxation opening to attach the plate to the bone. When attaching means contacting surface 32 is initially disposed against the outer surface of the attaching means, there preferably are no gaps or voids between attaching means contacting surface 32 and the outer surface of the attaching means. Attaching means contacting surface 32 is preferably configured to face generally oppositely to plate contacting surface 30.

As shown for example in FIG. 5, polymer member 28 preferably covers all of the plate opening surface, and attaching means contacting surface 32 preferably is configured to conform to the outer surface 33 of the attaching means which resides within the relaxation plate opening when the attaching means is inserted therethrough and secured to the bone. The thickness profile of polymer member 28 preferably is substantially uniform at the initial stage of its reception into a respective relaxation opening.

Figure 3:
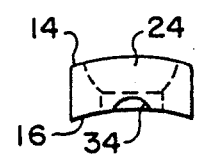
FIG. 3 is a side elevation view taken along the lines 3—3 of FIG. 1.

In the embodiments of the plate shown in FIGS. 1-3, the longitudinal dimension of the plate corresponds to the longitudinal dimension of the bone to which the plate is to be attached. Accordingly, when attached to the bone, the plate will be disposed so that the fracture lies generally transverse to the longitudinal dimension of the plate and between openings 20 and 22 in the plate shown in FIGS. 1 and 2. Moreover, in the embodiment of the plate shown in FIGS. 1 and 2, the load is intended to be carried by the longitudinal dimension of the plate.

Figure 6:
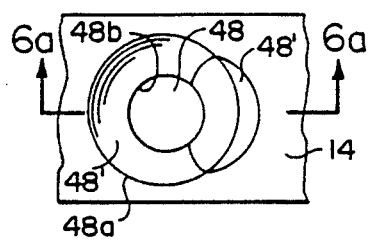
FIG. 6 is a partial top plan elevation view of an alternative preferred embodiment of a component of the present invention.
Figure 6A:
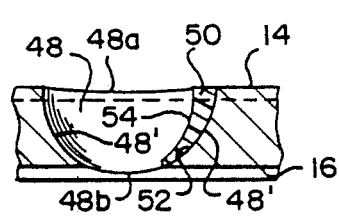
FIG. 6a is a cross-section view taken along the lines 6a—6a of the alternative preferred embodiment shown in FIG. 6.

In some alternative preferred embodiments such as shown in FIGS. 6 and 6a, the polymer member contacts less than all, a quarter for example, of the circumference of a specially configured relaxation plate opening 48. In this embodiment, the polymer member acts as a partial lining between plate opening surface 48' and the attaching means. When the plate carries the load in such partial lining embodiments, a polymer member 50 is disposed so that the load carried by the plate causes the attaching means to press against that portion of the plate opening surface which is covered by polymer member 50.

Polymer member 50 has a plate contacting surface 52 that is configured to contact plate opening surface 48' of a respective relaxation opening 48 in an uninterrupted fashion from the top plate surface to the bottom plate surface. When plate contacting surface 52 of polymer member 50 is disposed against plate opening surface 48' for example, there initially are preferably no gaps or voids between plate contacting surface 52 and plate opening surface 48'. In other words, as shown in FIG. 6a, all of plate contacting surface 52 of polymer member 50 is preferably disposed against at least a continuous portion of plate opening surface 48'.

As shown for example in FIG. 6a, polymer member 50 also has an attaching means contacting surface 54 which is disposed to contact the attaching means, such as a screw, when device 10 is in use for bone fracture healing. Attaching means contacting surface 54 is preferably configured to conform to at least the continuous portion of the outer surface of the attaching means that resides within the relaxation opening when the attaching means extends through the relaxation opening to attach the plate to the bone. When attaching means contacting surface 54 is initially disposed against the outer surface of the attaching means, there preferably are no gaps or voids between attaching means contacting surface 54 and the outer surface of the attaching means. Attaching means contacting surface 54 is preferably configured to face generally oppositely to plate contacting surface 52.

As can be determined from viewing FIGS. 6 and 6a, polymer member 50 can be configured as a crescent-shaped spherical section. Relaxation opening 48 is configured to receive polymer member 50 preferably such that the overall configuration of the opening formed by the combination of on the one hand the uncovered portion of opening surface 48' of relaxation opening 48 and on the other hand the attaching means contacting surface 54 of polymer member 50, is a sphere truncated at two opposing ends such that the holes 48a, 48b formed at the two truncation sites are concentric circles.

When the polymer member is initially placed into a relaxation opening, opening 18 for example, the polymer member preferably has a substantially uniform thickness profile above plate opening surface 18' for example. The thickness profile of the polymer member can be varied, as will become apparent, depending upon the application. The extent of coverage of the polymer member over the plate opening surface of the relaxation opening also can be varied, depending upon the application.

The attaching means, such as a self-tapping screw generally designated 35 in FIG. 5, will be carried at least partially by polymer member 28 when the attaching means is passed through a relaxation plate opening and embedded into the bone tissue while device 10 is in use to aid healing of bone fractures. Thus, each polymer member will carry part of the load carried by plate 12 when the device is in use to relieve the fractured bone from carrying loads during healing.

When plate 12 is attached to the bone, the bone is in a compressed state, and plate 12 is in tension due to the so-called self-compression of the bone caused by the screws and device 10. The self-compression is achieved by making predrilled screw holes, such as hole 37 shown in phantom in FIG. 5, in the bone with a template. The holes are placed slightly farther apart than openings 20, 22 are spaced from one another in plate 12. Thus, when the screws are tightened into openings 20, 22, the spherically shaped screw heads will force the bone to be compressed and plate 12 to be in tension.

In operation, the thickness profile of the polymer member gradually changes to change the separation between the attaching means and the relaxation opening through which the attaching means extends during attachment of the plate to the bone. This change in the thickness profile can result from a decrease in the thickness of the polymer member. To the extent that the thickness decreases over a period of time, a gradual decrease occurs in the load carried by device 10, and an increase occurs in the load carried by the bone to which device 10 is attached. This is accomplished in one of two ways depending upon the composition of the polymer member.

The polymer member is formed preferably either of viscoelastic material or resorbable material. When formed of a viscoelastic material, the polymer is preferably ultra high molecular weight polyethelyne (UHMWPE) of a type that has been approved by the U.S. Food & Drug Administration for use in prosthetic hip joints. When formed of a resorbable material, the polymer member is preferably formed of polyglycolic acid or polylactic acid such aas used for sutures approved by the U.S. Food and Drug Administration.

When viscoelastic material composes the polymer member, this material deforms under load and creeps out of the relaxation opening and over top surface 14 of plate 12. In this way, the section of the attaching means contacting surface near the top of the attaching means moves away from the gapless contact with the attaching means that characterized the initial installation of device 10 to the fractured bone. Thus, a change in the thickness profile of the polymer member between the upper portion of the attaching means and the opening surface of the relaxation opening occurs. This in turn results in a loosening of the fit of the attaching means in the opening formed by the attaching means contacting surface of the polymer member. Accordingly, as the fit becomes looser, the device gradually transfers load to the bone during the healing process and substantially prevents the stress-shielding of the bone that occurs with the use of conventional bone fracture plates. The substantial prevention of the undesirable stress-shielding effect of conventional bone fracture plates eliminates, or significantly reduces, the incidence of osteoporosis and osteopenia.

When resorbable material composes the polymer member, the body tissue surrounding device 10 gradually absorbs this material. This reduces the size of the polymer member and results in a reduced thickness profile of the polymer member between the attaching means and the plate opening surface of the relaxation opening. Thus, both the thickness profile of the polymer member and the separation between the attaching means and the opening surface change.

It is important to control the rate at which the fit of the attaching means in the opening becomes loose, because this rate determines when and to what extent the load is transferred from the plate to the healing bone. If too much load is transferred too soon, the bone will not heal properly. If too little load is transferred or the load is transferred too late, then the conditions sought to be prevented by the invention, namely, osteoporosis and osteopenia, will begin to occur.

Reliable operation of the device of the present invention requires a predictable rate of transferring the load from the plate to the bone. The attainment of reliable and predictable rates of load transfer are further promoted by the combined structure formed by plate 12, the polymer member, the attaching means, and the surface of the bone contacting bottom surface 16 of plate 12 when the device is in use. As best shown by referring to FIG. 5 for example, the end of polymer member 28 terminating at bottom surface 16 is trapped and prevented from moving by the seal provided by the combined structure of the bone 17, opening surface 20 and the outer surface of the attaching means. Thus, if creep is to occur, it must occur from around the edge of the attaching means near top surface 14 of plate 12. Since creep rates for UHMWPE are predictable, giving due consideration to the configuration and dimensions of the polymer member and the stresses applied when the plate is attached to the bone, the rate of creep can be controlled and accordingly the period of time over which the load is transferred from the plate to the bone can be controlled.

For one embodiment of the present invention, the long term change in the tensile strain to which a plate such as used in the present invention is subjected during bone healing, has been tabulated in TABLE 1.

TABLE 1
RESULTS OF TENSILE STRAIN WITH TIME

| Time (Hr.) | Strain ($\times 10^{-6}$) | Strain Change ($\times 10^{-6}$) | Strain Ratio* |
|---|---|---|---|
| 0.00 | 644.00 | 0.00 | 0.000000 |
| 0.12 | 623.00 | 21.00 | 0.032609 |
| 0.48 | 607.00 | 37.00 | 0.057453 |
| 1.05 | 596.00 | 48.00 | 0.074534 |
| 17.83 | 551.00 | 93.00 | 0.144410 |
| 28.82 | 548.00 | 96.00 | 0.149068 |
| 41.05 | 530.00 | 114.00 | 0.177019 |
| 48.68 | 524.00 | 120.00 | 0.186335 |
| 91.02 | 516.00 | 128.00 | 0.198758 |
| 149.47 | 496.00 | 148.00 | 0.229814 |
| 211.18 | 492.00 | 152.00 | 0.236025 |
| 235.50 | 484.00 | 160.00 | 0.248447 |
| 260.60 | 481.00 | 163.00 | 0.253106 |

The TABLE 1 data has been correlated into a mathematical relation (Equation 1) obtained using curve fitting techniques. Equation 1; $\mathrm{Log}\,(\Delta E/E_0) = -1.14 + 0.275T - 0.773T^2 + 0.043T^3 - 0.0052T^5 + 0.00031T^7$ where $\Delta E$ is the change in strain, $E_0$ is the initial strain (644 $\mu\epsilon$) and T is the log of the time elapsed from the initial strain $E_0$ reading. Using Equation 1, 61.5% of the initial tensile strain has been predicted to be relaxed after a three-month period, and 84.76% of the initial tensile strain has been predicted to be relaxed after a four-month period. These results are shown below in TABLE 2.

TABLE 2
PREDICTED LONG-TERM STRAIN RELAXATION

| Time (Hr.) | Strain ($\times 10^{-6}$) | Strain Change ($\times 10^{-6}$) | Strain Ratio* |
|---|---|---|---|
| 2160.00 (3 mos.) | 247.83** | 396.17 | 0.615000 |
| 2880.00 (4 mos.) | 96.16** | 545.84 | 0.847600 |

*change in strain divided by initial strain
**predicted values based on log correlation of data Reliable and predictable control over the rate of load transfer is also effected when the polymer member is composed of resorbable material. However, in this case, the primary avenue for absorption of the resorbable material into the body is the site where the polymer member extends to the top surface of plate 12. Resorbable materials are less readily absorbed by bone tissue than by the body tissues present near top surface 14. Removal of resorbable material from the portion of the polymer member nearest top surface 14 of plate 12 produces a gap between the outer surface of the attaching means and the attaching means contacting surface of the polymer member.

The desired thickness of the polymer member and the desired extent of coverage by the polymer member over each opening surface 18', 20', 48' of each respective relaxation opening 18, 20, 48 depend upon such factors as the size and shape of the plate, the number of relaxation openings, the degree of initial compression on the bone, whether the relaxation openings are of one type 18, 20, or another type 48, and the mix of the types of relaxation openings, etc.

EXAMPLE

Conventional four-hole compression bone plate (Zimmer 2462-04) and newly designed bone plates fitted with a polymer member in two screw holes on one side of the plate were implanted on the lateral sides of the femurs of adult mongrel dogs under general anesthesia, using aseptic surgical techniques. The polymer member in each screw hole was 1 mm. thick and composed of UHMWPE. The polymer member covered less than half of the hole surface and extended continuously from the top surface of the plate to the bottom surface of the plate. Templates were used to control the exact location of the screw holes for controlled compression on the bone. After 3 months, the femurs were harvested. For the three-point bending test, the four specimens were cut at 4 different quadrants from the mid-portion where the bone plate was attached. Under wet conditions, each specimen was ground to a rectangular shape. All specimens were stored in saline solution before testing on the same day of sacrificing. The cross-head speed of the MTS materials testing machine was 0.2 cm/min and the span was 36 mm.

Using the Eyecom Image Analyzing Processor, the volume fraction of pores was determined at the three positions between four screw holes of the longitudinal cross section from the x-ray microradiographs of thin sections (50 microns) of the bone. Cortical thickness also was measured using a precision dial caliper.

A summary of the mechanical tests, percent porosity and cortical bone thickness measurements are given in TABLE 3. Due to the limited number of samples, no statistically significant results could be obtained for all the parameters. However, there appears to be a trend which shows that the modulus of elasticity and cortical bone thickness are higher for the newly designed bone plates of the present invention than for conventional bone plates. No differences could be obtained for the ultimate flexural strength and the percent porosity.

The following explanation is provided to understand the presentation in TABLE 3 which follows. The polymer member is disposed on the lateral side and not on the medial side of the holes. The mean ± confidence limit is ($t\sigma/\sqrt{n}$), where the numbers in parenthesis indicate the number of samples. Regarding the confidence limit parameters, t is student t value for α=5%; σ is mean, and n is number of samples.

TABLE 3

| SUMMARY OF RESULTS | | |
| --- | --- | --- |
| | Lateral | Medial |
| Plate of the Present Invention | | |
| Modulus of Elasticity (GPa) | 16.2 ± 3.0(8) | 18.8 ± 2.0(8) |
| Ultimate Flexibility Strength (MPa) | 194.6 ± 25.0(8) | 209.0 ± 21.2(8) |
| Porosity (Volume %) | 11.5 ± 3.8(12) | 8.5 ± 3.9(12) |
| Cortical Thickness (mm) | 2.9 ± 0.5(6) | 3.7 ± 0.4(6) |
| Conventional Plate | | |
| Modulus of Elasticity (GPa) | 14.3 ± 3.1(8) | 16.4 ± 1.7(8) |
| Ultimate Flexibility Strength (MPa) | 194.3 ± 38.0(8) | 214.7 ± 19.8(8) |
| Porosity (Volume %) | 8.8 ± 3.4(12) | 10.2 ± 6.0(12) |
| Cortical Thickness (mm) | 2.6 ± 0.3(6) | 2.9 ± 0.2(6) |

It will be apparent to those skilled in the art that various modifications and variations can be made in the non-stress shielding bone fracture plate of the present invention without departing from the scope or spirit of the invention. For example, the plate can be curved instead of flat and shaped differently than the one illustrated in the figures. Thus, it is intended that the present invention cover the modifications and variations of this invention provided they come within the scope of the appended claims and their equivalents.

What is claimed is:

1. A non-stress-shielding bone fracture compression healing device to be used with a means for attaching same to bone tissue having a fracture therein, the attaching means having an outer surface facing its environment, the device comprising:
   a rigid plate having a length, a width, a height, a top surface, a bottom surface and a predetermined region extending along the length thereof intended to be disposed so as to extend across the bone fracture;
   at least two openings defined in said plate and extending through said plate from said top surface to said bottom surface, said predetermined plate region being disposed between at least said two openings;
   each said opening having an opening surface defining the boundary of said opening through said plate from said top plate surface to said bottom plate surface; and
   at least one of said openings being a relaxation opening, for each said relaxation opening, means for producing a separation between at least a portion of the outer surface of the attaching means and at least a portion of said opening surface of said relaxation opening when the attaching means extends through said relaxation opening to attach said plate to the bone tissue, said separation producing means having a thickness profile, said thickness profile being controllable to change said thickness profile gradually over a predetermined period of time, said gradual change in said thickness profile causing gradual transfer of load from said plate and attaching means to the bone attached to said plate.

2. A device as in claim 1, wherein
   each said relaxation opening having an entrance hole through said top plate surface and an exit hole through said bottom plate surface, said opening surface of each said relaxation opening being configured as a sphere truncated at said entrance hole and said exit hole; and
   said rigid plate is formed of biocompatible metal.

3. A device as in claim 2, wherein said separation producing means comprises:
   a viscoelastic polymer member received in each said relaxation opening, each said polymer member having a plate contacting surface configured to contact said opening surface of said relaxation opening from said top plate surface to said bottom plate surface; and
   each said polymer member having an attaching means contacting surface configured to contact the portion of said outer surface of said attaching means that resides within said relaxation opening when the attaching means extends through said relaxation opening to attach said plate to the bone.

4. A device as in claim 3, wherein said viscoelastic polymer is ultra high molecular weight polyethylene; and
   all of said plate contacting surface of said viscoelastic polymer member being disposed against at least a continuous portion of said opening surface of said relaxation opening.

5. A device as in claim 3, wherein said polymer member defines an entrance concentric with said entrance hole of said relaxation opening and said polymer member further defines an exit concentric with said exit hole of said relaxation opening.

6. A device as in claim 2, wherein said separation producing means comprises:
   a resorbable polymer member received in each said relaxation opening, each said polymer member having a plate contacting surface configured to contact said opening surface of said relaxation opening from said top plate surface to said bottom plate surface; and
   each said polymer member having an attaching means contacting surface configured to contact the portion of said outer surface of said attaching means that resides within said relaxation opening when the attaching means extends through said relaxation opening to attach said plate to the bone.

7. A device as in claim 6, wherein said resorbable polymer is polyglycolic acid; and
   all of said plate contacting surface of said polymer member being disposed against at least a continuous portion of said plate opening surface of said relaxation opening.

8. A device as in claim 7, wherein:
   said portion of said opening surface contacted by and disposed against said plate contacting surface of said polymer member being all of said opening surface.

9. A device as in claim 8, wherein said polymer member defines an entrance concentric with said entrance hole of said relaxation opening and further defines an exit concentric with said exit hole of said relaxation opening.

10. A device as in claim 6, wherein said resorbable polymer is polylactic acid.

11. A device as in claim 10, wherein:
    said portion of said plate opening surface contacted by and disposed against said plate contacting surface of said polymer member being all of said plate opening surface.

12. A device as in claim 11, wherein said rigid plate is formed of corrosion resistant metal.

13. A device as in claim 10, wherein said polymer member defines an entrance concentric with said entrance hole of said relaxation opening and further defines an exit concentric with said exit hole of said relaxation opening.

14. A device as in claim 2, wherein:
said plate has two relaxation openings disposed on the same side of said predetermined plate region.

15. A device as in claim 1, wherein:
said portion of said opening surface contacted by and disposed against said plate contacting surface of said polymer member being less than all of said opening surface.

16. A device as in claim 15, wherein:
a generally spherically shaped surface is formed in part by said opening surface and in remaining part by said attaching means contacting surface of said polymer member.

17. A device as in claim 15, wherein:
said polymer member being configured as a crescent-shaped spherical section.

18. A none-stress-shielding bone fracture compression healing device to be used with a means for attaching same to bone tissue having a fracture therein, the attaching means having an outer surface facing its environment, the device comprising:
 a rigid plate having a length, a width, a height, a top surface, a bottom surface, and a predetermined region extending along the length thereof intended to be disposed so as to extend across the bone fracture;
 at least two openings defined in said plate and extending through said plate from said top surface to said bottom surface, said predetermined plate region being disposed between at least said two openings;
 each said opening having an opening surface defining the boundary of said opening through said plate from said top plate surface to said bottom plate surface;
 at least one of said openings being a relaxation opening, each said relaxation opening having an entrance hole through said top plate surface and an exit hole through said bottom plate surface, said opening surface of each said relaxation opening being configured as a sphere truncated at said entrance hole and said exit hole;
 a viscoelastic polymer member received in each said relaxation opening, each said polymer member having a plate contacting surface configured to contact said opening surface of said relaxation opening from said top plate surface to said bottom plate surface;
 each said polymer having an attaching means contacting surface configured to contact the portion of said outer surface of said attaching means that resides within said relaxation opening when the attaching means extends through said relaxation opening to attach said plate to the bone; and
 said polymer member having a thickness, said thickness being controllable to change gradually over a predetermined period of time to thereby cause gradual transfer of load from said plate and attaching means to the bone attached to said plate.

19. A non-stress-shielding bone fracture compression healing device to be used with a means for attaching same to bone tissue having a fracture therein, the attaching means having an outer surface facing its environment, the device comprising:
 a rigid plate having a length, a width, a height, a top surface, a bottom surface, and a predetermined region extending along the length thereof intended to be disposed so as to extend across the bone fracture;
 at least two openings defined in said plate and extending through said plate from said top surface to said bottom surface, said predetermined plate region being disposed between at least said two openings;
 each said opening having an opening surface defining the boundary of said opening through said plate from said top plate surface to said bottom plate surface;
 at least one of said openings being a relaxation opening, each said relaxation opening having an entrance hole through said top plate surface and an exit hole through said bottom plate surface, said opening surface of each said relaxation opening being configured as a sphere truncated at said entrance hole and said exit hole;
 a resorbable polymer member received in each said relaxation opening, each said polymer member having a plate contacting surface configured to contact said opening surface of said relaxation opening from said top plate surface to said bottom plate surface;
 each said polymer member having an attaching means contacting surface configured to contact the portion of said outer surface of said attaching means that resides within said relaxation opening when the attaching means extends through said relaxation opening to attach said plate to the bone; and
 said polymer member having a thickness, said thickness being controllable to change gradually over a predetermined period of time to thereby cause gradual transfer of load from said plate and attaching means to the bone attached to said plate.

* * * * *